United States Patent [19]
Truong et al.

[11] Patent Number: 6,025,337
[45] Date of Patent: Feb. 15, 2000

[54] SOLID MICROPARTICLES FOR GENE DELIVERY

[75] Inventors: Vu L. Truong; Thomas August, both of Baltimore; Kam W. Leong, Ellicot City, all of Md.

[73] Assignee: Johns Hopkins University, Baltimore, Md.

[21] Appl. No.: 08/657,913

[22] Filed: Jun. 7, 1996

Related U.S. Application Data

[63] Continuation of application No. 08/265,966, Jun. 27, 1994, abandoned.

[51] Int. Cl.$^7$ .......................... C12N 15/00; A01N 43/04
[52] U.S. Cl. ..................... 514/44; 435/320.1; 435/440; 435/455
[58] Field of Search ................ 514/2, 44; 435/172.3, 435/240.1, 320.1, 440, 455; 424/93.21

[56] References Cited

U.S. PATENT DOCUMENTS

| | | | |
|---|---|---|---|
| 4,885,172 | 12/1989 | Bally et al. | 424/417 |
| 4,948,590 | 8/1990 | Hawrot et al. | 424/450 |
| 5,008,116 | 4/1991 | Cahn | 424/491 |
| 5,166,319 | 11/1992 | Wrasidlo | 530/391.1 |
| 5,216,130 | 6/1993 | Line et al. | 530/362 |
| 5,258,499 | 11/1993 | Konigsberg et al. | 530/351 |
| 5,279,833 | 1/1994 | Rose | 424/450 |
| 5,393,527 | 2/1995 | Malick et al. | 435/7.1 |
| 5,635,383 | 6/1997 | Wu et al. | 435/172.3 |
| 5,661,025 | 8/1997 | Szoka, Jr. et al. | 435/172.3 |

FOREIGN PATENT DOCUMENTS 9417786  8/1994  WIPO.

OTHER PUBLICATIONS

Miller et al., FASEB journal, 9, 1995, 190–199.
Hodgson, Exp. Opin., Ther. Pat., 5(5), 1995, 459–468.
Davis et al., J. Controlled Rel., 24, 1993, 157–163.
Cortesi et al., Int. J. Pharmaceut., 105, 1994, 181–186.
Culver et al, TIG, 10(5), May 1994, 174–178.
Marshall, Science, 269, 1995, 1050–1055.
Truong et al., Exp. Biology, 1993, Abstract No. 30838.
Leong et al., Exp. Biology, 1993, Abstract No. 30839.
Gao et al, J. Liposome Res., 3(1), 1993, 17–30.
Verrijk et al., Cancer Chemo. Pharmacol., 29, 1991, 117–121.
Eldridge et al., Mol. Immunol., 28(3), 1991, 287–294.
Truong et al., Proc. Int. Symp. Control. Rel. Biact. Mater., 20:474–475, 1993.

*Primary Examiner*—Brian R. Stanton
*Assistant Examiner*—Deborah J. R. Clark
*Attorney, Agent, or Firm*—Banner & Witcoff, Ltd.

[57] ABSTRACT

A target-specific gene delivery system is made of enzymatically degradable gelatin and nucleic acids (DNA or RNA) microparticles with a linking moiety or a targeting ligand attached to the surface. The delivery system can be made by a simple method. Targeting ligands can be attached to the microparticle directly or via a linking moiety. The linkage design allows the attachment of any molecule onto the microparticle surface including antibodies, cell adhesion molecules, hormones and other cell-specific ligands.

40 Claims, 8 Drawing Sheets

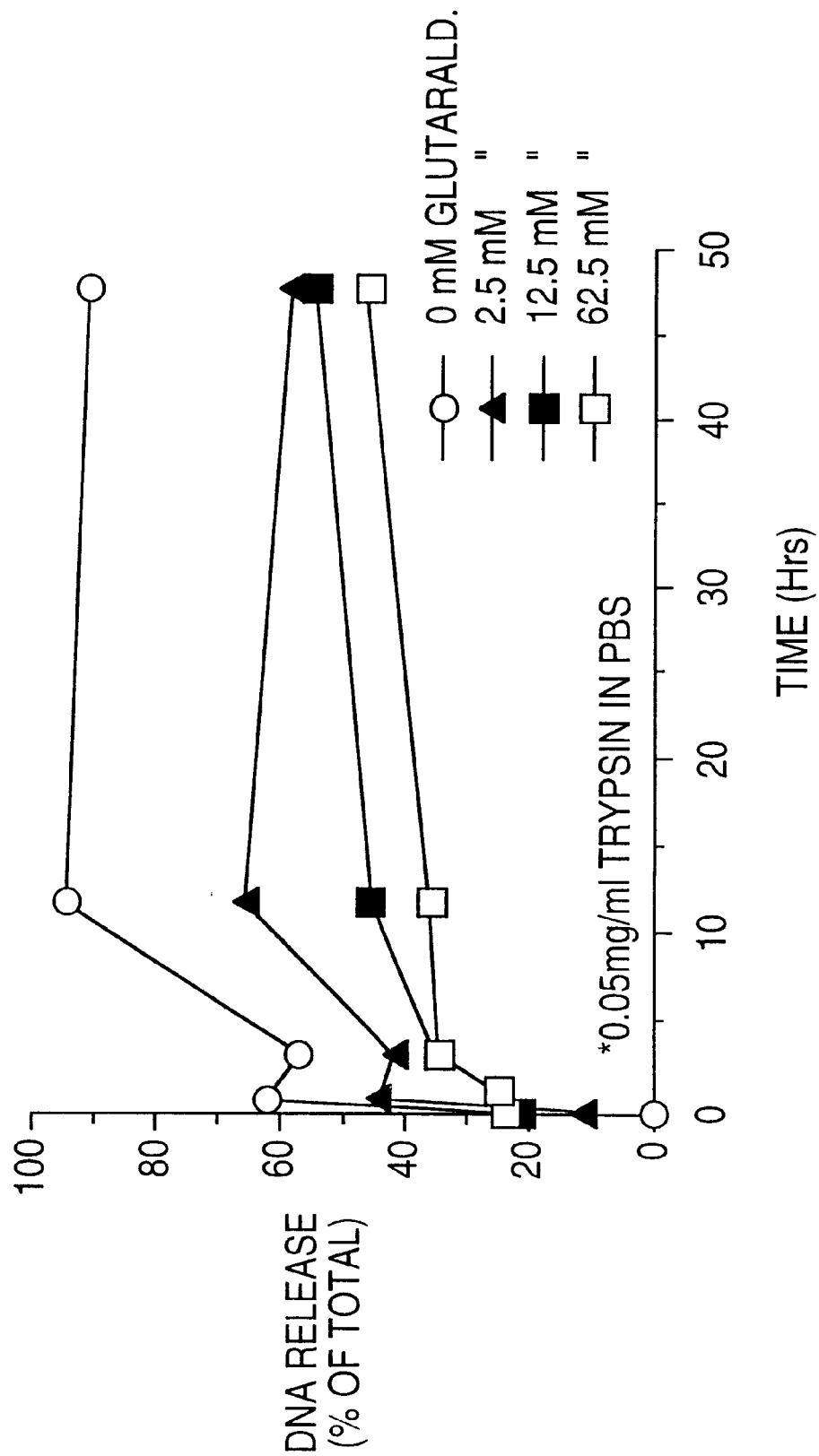

SOLID MICROPARTICLES FOR GENE DELIVERY

This application is a continuation of application Ser. No. 08/265,966, filed Jun. 27, 1994, now abandoned.

BACKGROUND OF THE INVENTION

A variety of techniques have been used to introduce foreign genes into cells. Physical methods include co-precipitation with calcium phosphate, electroporation, and particle bombardment. While these direct transfer techniques are adequate in vitro, they are impractical in vivo. Promising in vivo gene therapy relies on a carrier such as viral vectors or liposomes for delivery. There are still lingering safety concerns for viral vectors. Another limitation is the size of the DNA sequences, usually limited to 7–8 kb, that can be incorporated into the viral vector. Liposomes, on the other hand, have low loading level in general. In both cases, there is the issue of cell or tissue specificity for these gene delivery systems.

Controlled drug delivery has significantly improved the success of many drug therapies (Langer, R., 1990, New methods of drug delivery, *Science*, 249:1527–33; Poznansky, et al., 1984, Biological approaches to the controlled delivery of drugs: a critical review, *Pharmacol. Rev.*, 36:277–336). A major goal of drug delivery is to localize the drug to the target site. These targeted delivery systems often take the form of injectables composed of liposomes (Gregoriadis, G., 1988, Liposomes as Drug Carriers, New York: Wiley; Litzinger, et al., 1992, Phosphatidylethanolamine liposomes: drug delivery, gene transfer and immunodiagnostic applications, *Biochimica et Biophysica Acta.*, 1113:201–27) and microspheres made of proteins (Cummings, et al., 1991, Covalent coupling of doxorubicin in protein microspheres is a major determinant of tumor drug deposition, *Biochem. Pharm.*, 41:1849–54; Verrijik, et al., 1991, Polymer-coated albumin microspheres as carriers for intravascular tumor targeting of cisplatin, *Cancer Chemother. and Pharm.*, 29:117–21; Tabata, et al., 1988, Potentiation of antitumor activity of macrophages by recombinant interferon alpha A/D contained in gelatin microspheres, *Jpn. J. Cancer Res.*, 79:636–646), polysaccharides (Rongved, et al., 1991, Crossed-linked, degradable starch microspheres as carriers of paramagnetic resonance imaging: synthesis, degradation, and relaxation properties, *Carbohydrate Res.*, 145:83–92; Carter, et al., 1991, The combination of degradable starch microspheres and angiotensin II in the manipulation of drug delivery in an animal model of colorectal metastasis, *British J. Cancer*, 65:37–9), and synthetic polymers (Davis, et al., 1984, Microspheres and Drug Therapy, *Amsterdam*; Eldridge, et al., 1991, Biodegradable microspheres as a vaccine delivery system, *Molec. Immunology*, 28:287–94; Pappo, et al., 1991, Monoclonal antibody-directed targeting of fluorescent polystyrene microspheres to Peyer's patch M cells, *Immunology*, 73:277–80). Polymeric systems share some of the advantages of liposomal systems such as altered pharmacokinetics and biodistribution. While liposomes might have better prospects of biocompatibility and potential for fusion with cells, polymeric microspheres have more controllable release kinetics, better stability in storage, and higher drug-loading levels for some classes of compounds.

We have previously synthesized microspheres by the complex coacervation of gelatin and chondroitin sulfate (Truong, et al., 1993, A target-specific microspheres drug delivery system made of enzymatically degradable gelatin and chondroitin sulfate coacervates, *Controlled Release Society*, Abstract #1336; Azhari, et al., 1991, Protein release from enzymatically degradable chondroitin sulfate/gelatin microspheres, *Intern. Symp. Control. Rel. Bioact. Mater.*, 18). These microspheres could be stabilized by cross-linking with glutaraldehyde, the extent of which controls the degradation and drug release rate. Biodegradability of these microspheres in serum is effected by presence of metalloproteinases such as gelatinase, collagenase, and trypsin.

Thus there is a need in the art for a targeted DNA delivery system which can provide controlled release, is simple to make, is stable, is cost effective, has a high DNA loading level, and is relatively non-immunogenic.

SUMMARY OF THE INVENTION

It is an object of the invention to provide polymeric particles for delivery of DNA to cells.

It is an object of the invention to provide a method of making polymeric particles for delivery of DNA to cells.

It is another object of the invention to provide a method of delivering DNA to cells using polymeric particles.

These and other objects of the invention are provided by one or more of the embodiments described below. In one embodiment a microparticle for gene delivery to specific targets is provided. The microparticle comprises gelatin and DNA, and a linking molecule or a targeting ligand is attached to the surface of said microparticle.

In another embodiment of the invention a method of forming microparticles for gene delivery to specific targets is provided. The method comprises the steps of: forming microparticles by coacervation of DNA and gelatin; and adhering a linking molecule or a targeting ligand to the surface of the microparticles.

In yet another embodiment of the invention a method for introducing genes into cells is provided. The method comprises incubating cells to be transfected with solid microparticles comprising gelatin and DNA, wherein a targeting ligand is attached to said microparticle's surface, said targeting ligand binding to the surface of said cells.

Thus the present invention provides the art with an attractive DNA delivery system which is simple to prepare, is cost effective, has controlled release ability, is storage stable, and is biocompatible.

BRIEF DESCRIPTION OF THE DRAWINGS

FIGS. 3(A–B). Controlled release of intact LAMP-1 cDNA was demonstrated in vitro. The microparticles were cross-linked with glutaraldehyde at various glutaraldehyde concentrations then degraded with trypsin.

FIG. 3A shows the time course of DNA release at various glutaraldehyde-cros-linking levels.

FIGS. 4(A–D). Fluorescent images of U937 cells transfected by controls and LAMP-1 cDNA-loaded microparticles (at day 3 post-transfection).

DETAILED DESCRIPTION OF THE PREFERRED EMBODIMENTS

Figure 1:
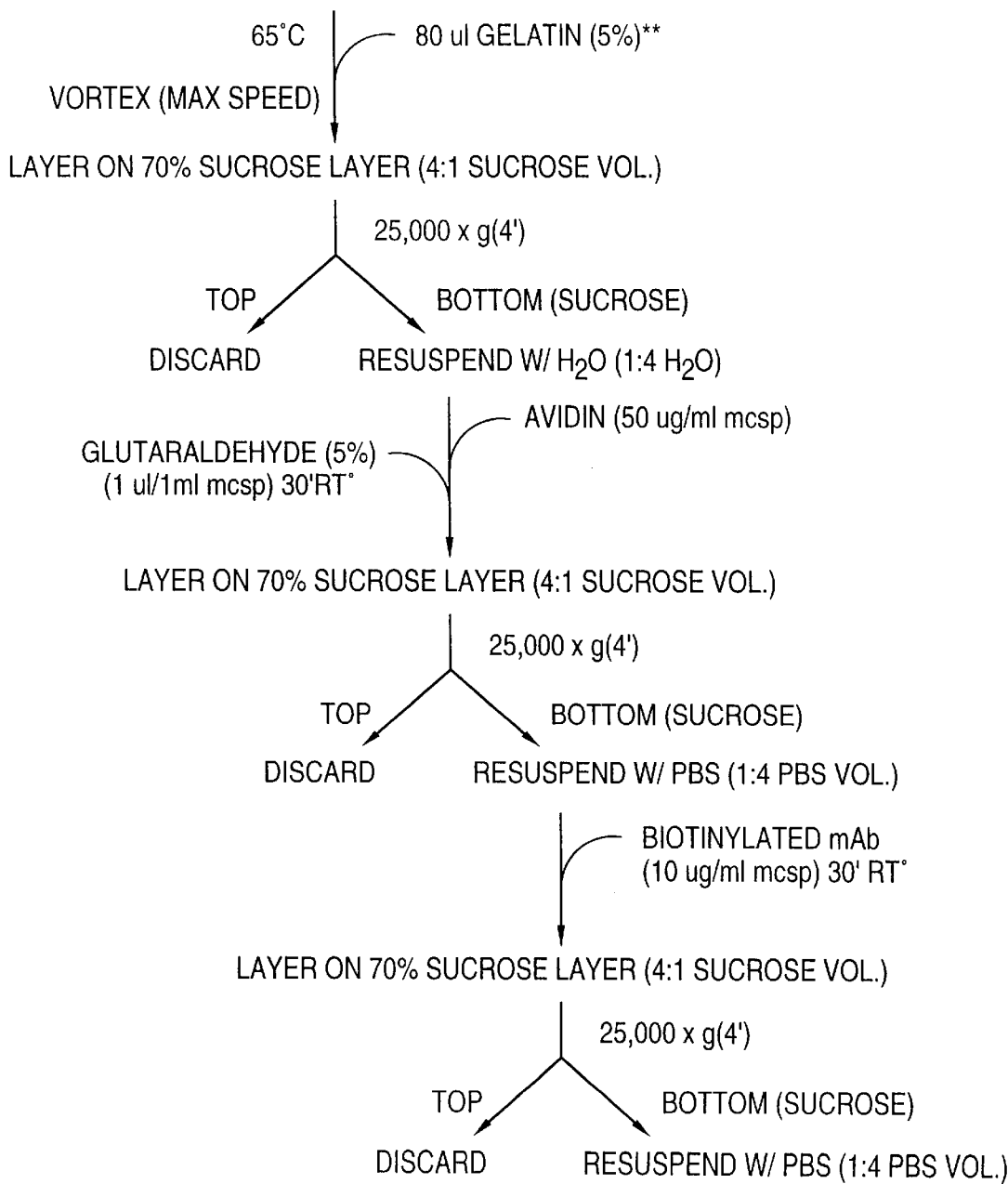
FIG. 1. Schematic diagram showing the synthesis of gelatin-DNA coacervates.

It is a discovery of the present invention that nucleic acid molecules of various chain lengths can complex with polymeric cations in aqueous conditions to form solid microparticles ranging from submicron to microns in size. These nucleic acid-loaded microparticles, when appropriately targeted, can transfect cells with phagocytic activity. The rate of microparticle degradation and nucleic acid release can be designed a priori by varying the extent of cross-linking. The loading level of nucleic acid can be as high as 30% (w/w), with an encapsulation efficiency of >95%.

According to the present invention, gelatin or other polymeric cation having a similar charge density to gelatin, is used to complex with nucleic acids to form microparticles. The source of gelatin is not thought to be critical; it can be from bovine, porcine, human, or other animal source. Typically the polymeric cation has a molecular weight of between 19,000–30,000. Poly-L-lysine may be particularly useful as the polymeric cation of the present invention. Desirably sodium sulfate is used to induce the coacervation of polymeric cation and nucleic acids. Ethanol can also be used at a concentration of about 40 to 60% to induce coacervation. Chondroitin sulfate can also be incorporated into the microparticle, which is especially beneficial if one desires other substances such as drugs to be incorporated in the microparticle. Typically the concentration of chondroitin sulfate is between about 0.005% and 0.1%.

Targeting ligands can be directly bound to the surface of the microparticle or can be indirectly attached using a "bridge" or "spacer". Because of the amino groups provided by the lysine groups of the gelatin, the surface of the microparticles can be easily derivatized for the direct coupling of targeting moieties. Alternatively, spacers (linking molecules and derivatizing moieties on targeting ligands) such as avidin-biotin can be used to indirectly couple targeting ligands to the microparticles. Biotinylated antibodies and/or other biotinylated ligands can be coupled to the avidin-coated microparticle surface efficiently because of the high affinity of biotin ($k_a$~$10^{15}M^{-1}$) for avidin (Hazuda, et al., 1990, Processing of precursor interleukin 1 beta and inflammatory disease, *J. Biol. Chem.*, 265:6318–22; Wilchek, et al., 1990, Introduction to avidin-biotin technology, *Methods In Enzymology*, 184:5–13). Orientation-selective attachment of IgGs can be achieved by biotinylating the antibody at the oligosaccharide groups found on the $F_C$ portion (O'Shannessy, et al., 1984, A novel procedure for labeling immunoglobulins by conjugation to oligosaccharides moieties, *Immunol. Lett.*, 8:273–277). This design helps to preserve the total number of available binding sites and renders the attached antibodies less immunogenic to $F_C$ receptor-bearing cells such as macrophages. Spacers other than the avidin-biotin bridge can also be used, as are known in the art. For example, Staphylococcal protein A can be coated on the microparticles for binding the $F_C$ portions of immunoglobulin molecules to the microparticles.

Cross-linking of linking molecules or targeting ligands to the microparticle is used to promote the stability of the microparticle as well as to covalently affix the linking molecule or targeting ligand to the microparticle. The degree of cross-linking directly affects the rate of nucleic acids release from the microshperes. Cross-linking can be accomplished using glutaraldehyde, carbodiimides such as EDC (1-ethyl-3-(3-dimethylaminopropyl)-carbodiimide, DCC (N,N'-dicyclohexylcarbodiimide),carboxyls(peptide bond) linkage,bis(sulfosuccinimidyl)suberate, dimethylsuberimidate, etc.

Targeting ligands according to the present invention are any molecules which bind to specific types of cells in the body. These may be any type of molecule for which a cellular receptor exists. Preferably the cellular receptors are expressed on specific cell types only. Examples of targeting ligands which may be used are hormones, antibodies, cell-adhesion molecules, saccharides, drugs, and neurotransmitters.

The microparticles of the present invention have good loading properties. Typically, following the method of the present invention, microparticles having at least 5% (w/w) nucleic acids can be achieved. Preferably the loading is greater than 10 or 15% nucleic acids. Often microparticles of greater than 20 or 30% nucleic acids can be achieved. Typically loading efficiencies of nucleic acids into microparticles of greater than 95% can be achieved.

The method of the present invention involves the coacervation of polymeric cations and nucleic acids. Because this process depends on the interaction of the positively charged polymeric cations and the negatively charged nucleic acids it can be considered as a complex coacervation process. However, sodium sulfate (or ethanol) induces the coacervation reaction by inducing a phase transition, and therefore it could also be considered as a simple coacervation reaction. Nucleic acids are present in the coacervation mixture at a concentration of between 1 ng/ml to 500 μg/ml. Desirably the nucleic acids are at least about 2–3 kb in length. Sodium sulfate is present at between 7 and 43 mM. Gelatin or other polymeric cation is present at between about 2 and 7% in the coacervation mixture.

An attractive microparticle delivery system requires a delicate balance among factors such as the simplicity of preparation, cost effectiveness, nucleic acids loading level, controlled release ability, storage stability, and immunogenicity of the components. The gene delivery system described here may offer advantages compared to other particulate delivery systems, including the liposomal system. The problems of instability, low loading level, and controlled release ability are better resolved with the polymeric microparticle systems. Gelatin has received increasing biologic use ranging from surgical tissue adhesive (Weinschelbaum, et al., 1992, Surgical treatment of acute type A dissecting aneurysm with preservation of the native aortic valve and use of biologic glue. Follow-up to 6 years, *J. Thorac. Cardiovasc. Surg.*, 130:369–74) to quantitative immunohistochemical assays (Izumi, et al., 1990, Novel gelatin particle agglutination test for serodiagnosis of leprosy in the field, *J. Clinical Microbiol.*, 28:525–9) and as drug delivery vehicle (Tabata, et al., 1991, Effects of recombinant alpha-interferon-gelatin conjugate on in vivo murine tumor cell growth, *Cancer Res.*, 51:5532–8), due to its biocompatibility and enzymatic degradability in vivo. Compared to other synthetic polymeric systems, such as the extensively studied polylactic/polyglycolic copolymers, the mild conditions of microparticle formulation are appealing. Unlike the solvent evaporation and hot-melt techniques used to formulate synthetic polymeric microparticles, complex coacervation requires neither contact with organic solvents nor heat. It is also particularly suitable for encapsulating bio-macromolecules such as nucleic acids not only through passive solvent capturing but also by direct charge-charge interactions.

Unlike viral vectors, which cannot deliver genes larger than 10 kb, the microparticle delivery system of the present invention does not have such size limitations. Nucleic acid molecules of greater than about 2 kb can be used, and nucleic acid molecules even greater than 10 kb may be used.

In general, the range of possible targets is dependent on the route of injection e.g. intravenous or intraarterial, subcutaneous, intra-peritoneal, intrathecal, etc. For systemic injections, the specificity of this delivery system is affected by the accessibility of the target to blood borne microparticles, which in turn, is affected by the size range of the particles. Size of the particles is affected by temperature, component concentration, and pH in the coacervation mixture. The particles can also be size-fractionated, e.g., by sucrose gradient ultracentrifugation. Particles with size less than 150 nanometers can access the interstitial space by traversing through the fenestrations that line most blood vessels walls. Under such circumstances, the range of cells that can be targeted is extensive. An abbreviated list of cells that can be targeted includes the parenchymal cells of the liver sinusoids, the fibroblasts of the connective tissues, the cells in the Islets of Langerhans in the pancreas, the cardiac myocytes, the Chief and parietal cells of the intestine, osteocytes and chrondocytes in the bone, keratinocytes, nerve cells of the peripheral nervous system, epithelial cells of the kidney and lung, Sertoli cells of the testis, etc. The targets for particles with sizes greater than 0.2 microns will be confined largely to the vascular compartment. Here, the targetable cell types include erythrocytes, leukocytes (i.e. monocytes, macrophages, B and T lymphocytes, neutrophils, natural killer cells, progenitor cells, mast cells, eosinophils), platelets, and endothelial cells.

For subcutaneous injections, the targetable cells includes all cells that resides in the connective tissue (e.g. fibroblasts, mast cells, etc.), Langerhans cells, keratinocytes, and muscle cells. For intrathecal injections, the targetable cells include neurons, glial cells, astrocytes, and blood-brain barrier endothelial cells. For intraperitoneal injection, the targetable cells include the macrophages and neutrophil.

EXAMPLES

Matrix Materials

Gelatin (60 bloom, type A from porcine skin), chondroitin 4-sulfate, glutaraldehyde (25%, grade 1), 1-ethyl-3-(3-dimethylaminopropyl)-carbodiimide hydrochloride (EDC hydrochloride), and ultra-pure sucrose were purchased from Sigma Chemical Co. (St. Louis, Mo.). Biotin LC hydrazide, and NeutrAvidin, and Coomassie protein assay reagents were from Pierce (Rockford, Ill.). Centricon microconcentrators were from Amicon (Beverly, Mass.).

Monoclonal antibodies mAb PLM-2, a BALB/c mouse anti-porcine LFA-1 ($IgG_{1k}$) which also cross reacts with murine LFA-1, was isolated and purified as previously described (Hildreth, et al., 1989, Monoclonal antibodies against porcine LFA-1: species cross-reactivity and functional effects of b-subunit-specific antibodies, *Molec. Immunol.*, 26:883–895). IB-4B, a rat anti-mouse LAMP-1 ascite fluid and a mouse anti-human CD44 mAb were isolated as previously described (de Wet, et al., 1987, Firefly luciferase gene: structure and expression in mammalian cells, *Mol. & Cell. Biol.*, 7:725–37). CHA is a $IgG_1$ that does not recognize any known in vivo mouse epitopes (Hybritech Inc., San Diego, Calif.). Affinity-purified FITC and Texas Red-labeled polyclonal anti-rat IgGs were obtained from Sigma.

Genes

Two genes were used to demonstrate the feasibility of this delivery system. The LAMP-a cDNA is a 6.4 kb circular supercoiled plasmid cDNA with a mouse LAMP-1 gene (2.4 kb) inserted into an Invitrogen plasmid cDNA with a CMV promoter (Guaarnieri, et al., 1993, *J. Biol. Chem.*, 268:1941). Detection of LAMP-1 expression was done by staining cells with anti-LAMP-1 mAb and with secondary anti-IgG mAb conjugated with Texas Red. The gene coding for luciferase enzyme is widely used in cell biology for the study of gene expression because of the high sensitivity of the assay, its simplicity, and low cost. In addition, the enzyme is a good reporter of gene expression because it is a cytosolic protein that does not require post-translational processing for enzymatic activity (de Wet, et al., 1987, Firefly luciferase gene: structure and expression in mammalian cells, *Mol. & Cell. Biol.*, 7:725–37; Wood, et al., 1989, Introduction to beetle luciferases and their applications, *J. of Biolumin. & Chemilum.*, 4:289–301). The presence of luciferase can be readily detected by an enzymatic reaction that involve the oxidation of beetle luciferin with concomitant production of a photon (in the form of chemiluminescence.) The assay was carried out using an assay kit purchased from Promega Corp. (Madison, Wis.).

Synthesis of microspheres

A detailed schematic diagram for the synthesis of the gelatin-DNA coacervates is shown in FIG. 1. All concentrations described are final concentrations in the reaction mixture set at 67° C. unless otherwise stated. Gelatin/plasmid DNA microparticles coated with avidin were synthesized by first preparing a 3.5 mg/ml solution of plasmid DNA encoding a lysosomal associated membrane protein-1 (LAMP-1) (6.7 Kb, circular supercoiled) in 42 mM sodium sulfate ($Na_2SO4$). Coacervation was initiated by the addition of gelatin (5%) to the DNA/$Na_2SO4$ solution at equal volume while vortexing at high speed for 1 minute. Coencapsulation of drugs and other agents can be achieved by adding directly to the DNA/$Na_2SO_4$ solution before initiating coacervation with gelatin. Avidin (5 mg/ml) was added to the microsphere suspension at a final concentration of 75 ug avidin/ml microsphere solution. The microspheres mixture was layered onto a layer of 70% sucrose (w/v) and centrifuged at 6,000 x g for 4 minutes (Brinkman Instruments Inc., Westbury, N.Y., model L8-75). Microsphere fractions recovered from the sucrose layer was diluted 5-fold with water then cross-linked with glutaraldehyde (12.5 mM final concentration) for 10 minutes at room temperature. Unreacted glutaraldehyde was quenched by adding ethanolamine (1 M) for 10 minutes. The microspheres were dialyzed by sucrose centrifugation as described above.

Attachment of biotinylated mAbs to avidin-coated microspheres 30 ug of antibodies (biotinylated according to established procedures (O'Shannessy, et al., 1984, A novel procedure for labeling immunoglobulins by conjugation to oligosaccharides moieties, *Immunol. Lett.*, 8:273–277)) was added to 1 ml of avidin-coated microspheres suspension (11 mg/ml) for 1 hour with gentle agitation. Unbound mAb was removed from microspheres by dialysis.

Characterization of microsphere and binding performance

Figure 2:
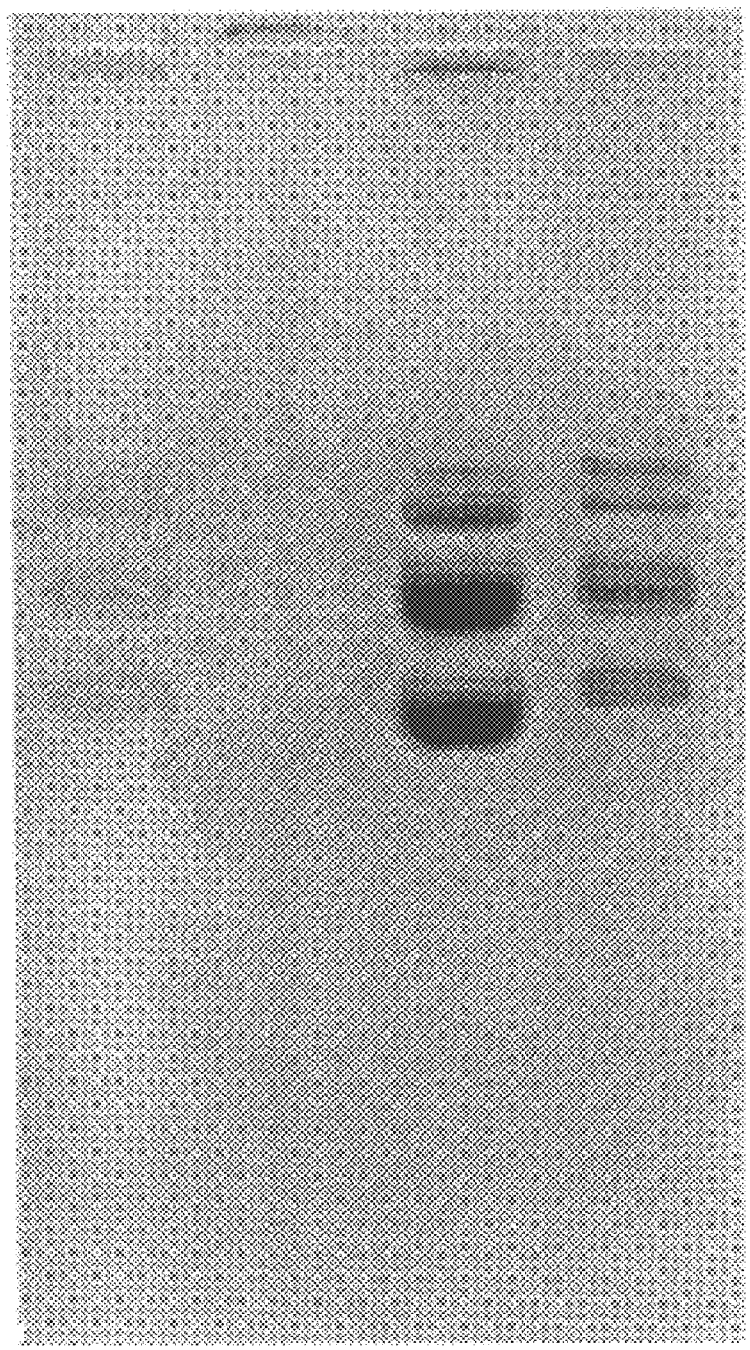
FIG. 2. Gel electrophoresis of cDNA before and after encapsulation. (std=standard; Sup=supernatant, Pellet=microparticles pelleted by centrifugation).
Figure 3B:
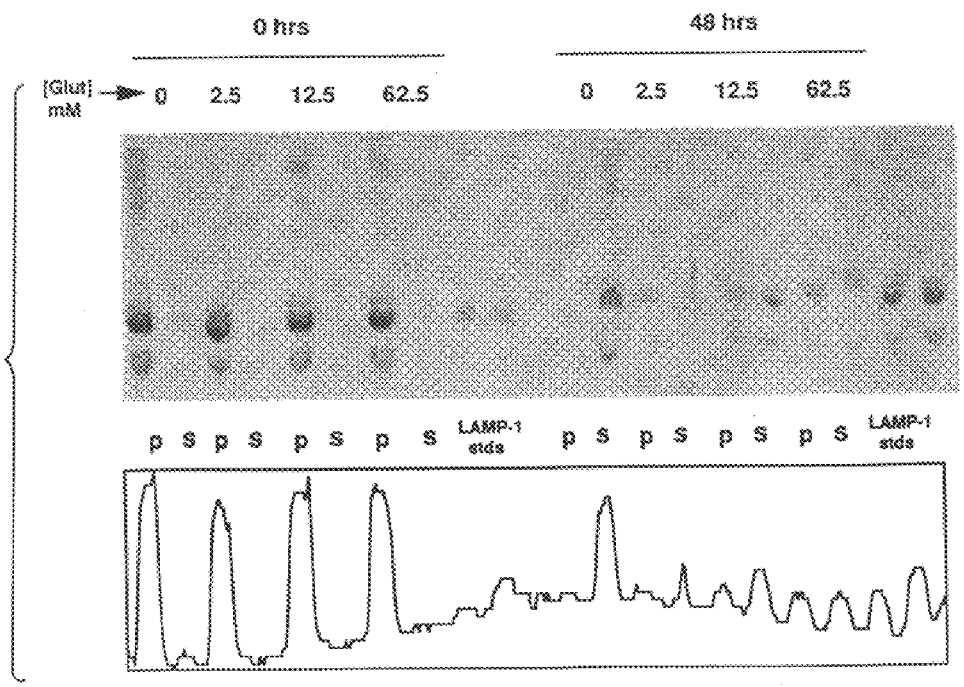
FIG. 3B shows (on gels and densitometer tracing) the DNA which was released from the microparticles at various times and at various levels of glutaraldehyde-cross-linking.

DNA loaded microspheres exhibited polymorphic colloid shape with a polydispersed particle size of less than 3 microns as determined by light microscopy. Purified microspheres were stable for at least one month without appreciable degradation. The loading level for LAMP-1 plasmid DNA was 20% (w/w). The encapsulation efficiency was typically >95%. The mobility of the free LAMP-1 DNA and the released DNA (from the microsphere) in 1% agarose gel electrophoresis were identical (FIG. 2), suggesting that the encapsulated DNA was released in its original form. Release rate of the cDNA from the microspheres was dependent on the crosslinking density and on the enzyme level (FIG. 4). Sustained release of up to weeks can be readily obtained.

Figure 4A:
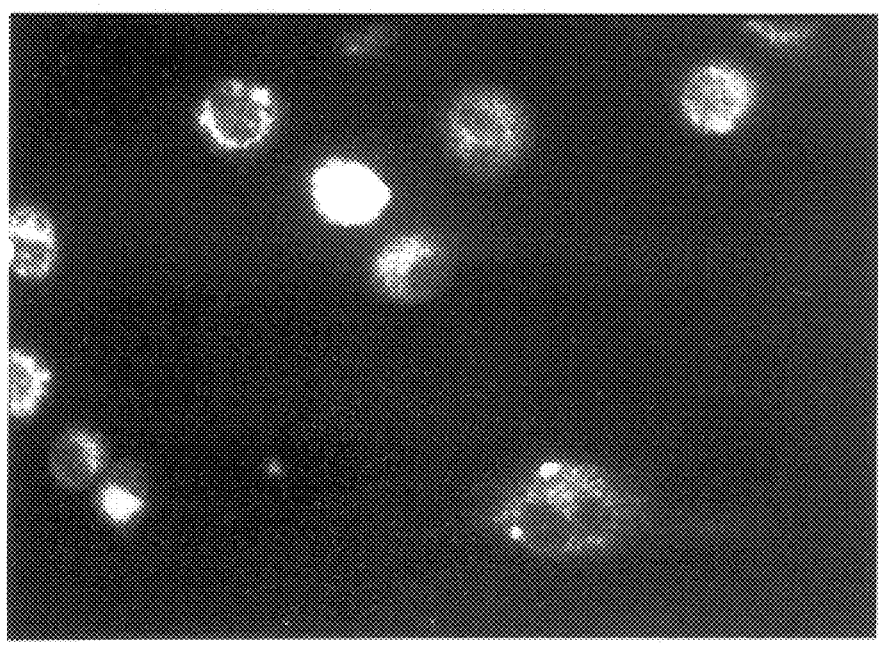
FIG. 4A: anti-DC44 microparticles without cDNA.
Figure 4B:
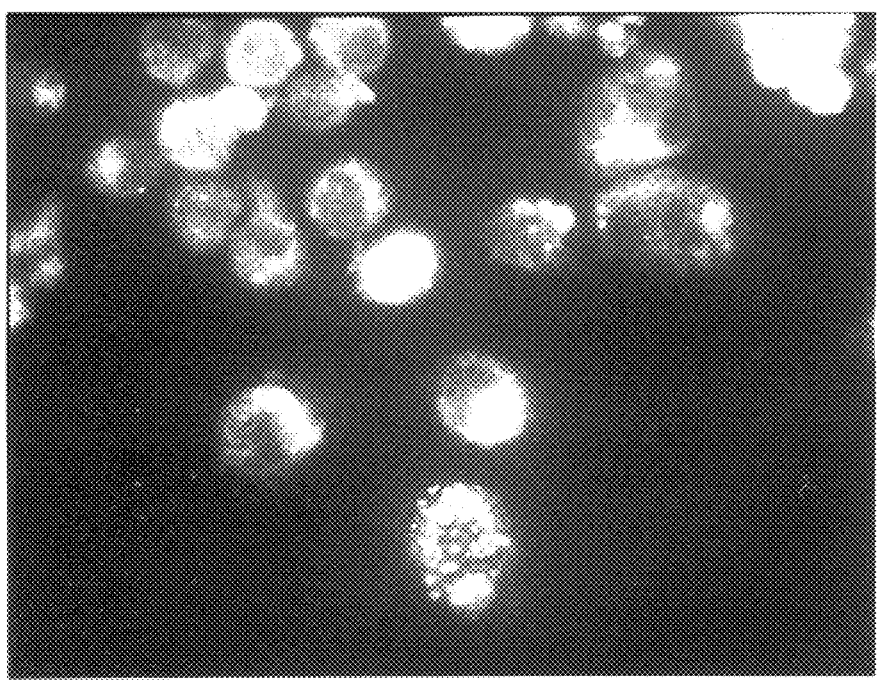
FIG. 4B: calcium phosphate transfection.
Figure 4C:
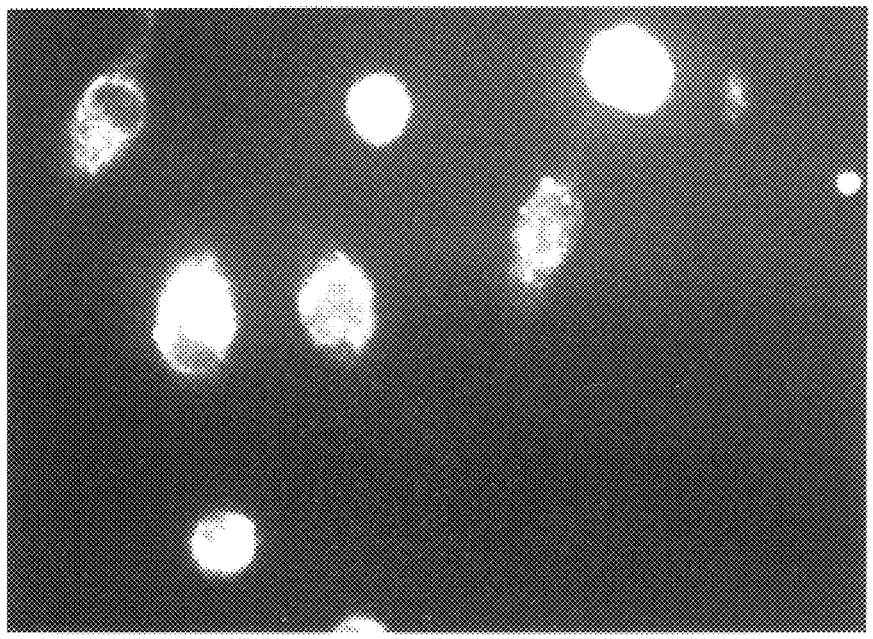
FIG. 4C: LAMP-1 microparticles without antibody.
Figure 4D:
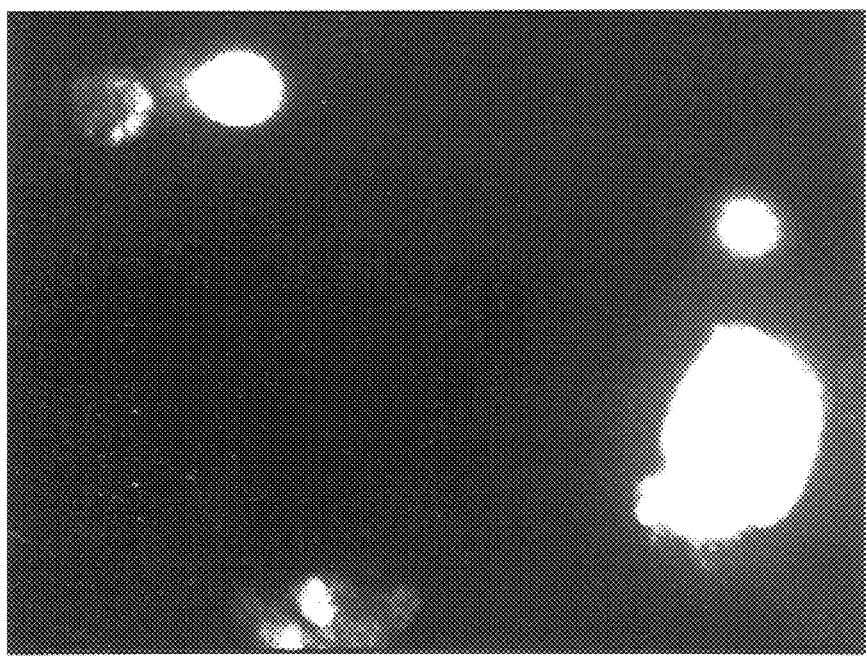
FIG. 4D: LAMP-1 microparticles coated with anti-CD-44 mAB. LAMP-1 expression is manifested as granules (in lysosomes) in the cells.

We tested the ability of the LAMP-1 DNA loaded microspheres to bind and subsequently transfect a human histiocytic lymphoma cell line (U937) in tissue culture. When coated with either anti-LFA or anti-CD44 monoclonal antibody (both protein targets were expressed in high amount of U937 cell surface), expression LAMP-1 protein was detected by day 3 (FIG. 4A, fluorescent granules) when stained with antibodies recognizing LAMP-1. The staining pattern of U937 cells incubated with LAMP-1 microspheres was identical to the calcium phosphate method of transfection (FIG. 4B). Microspheres that were either coated with avidin or non-specific CHA mAb showed no granular staining patterns, and were identical to untreated cells (FIG. 4C).

Figure 5:
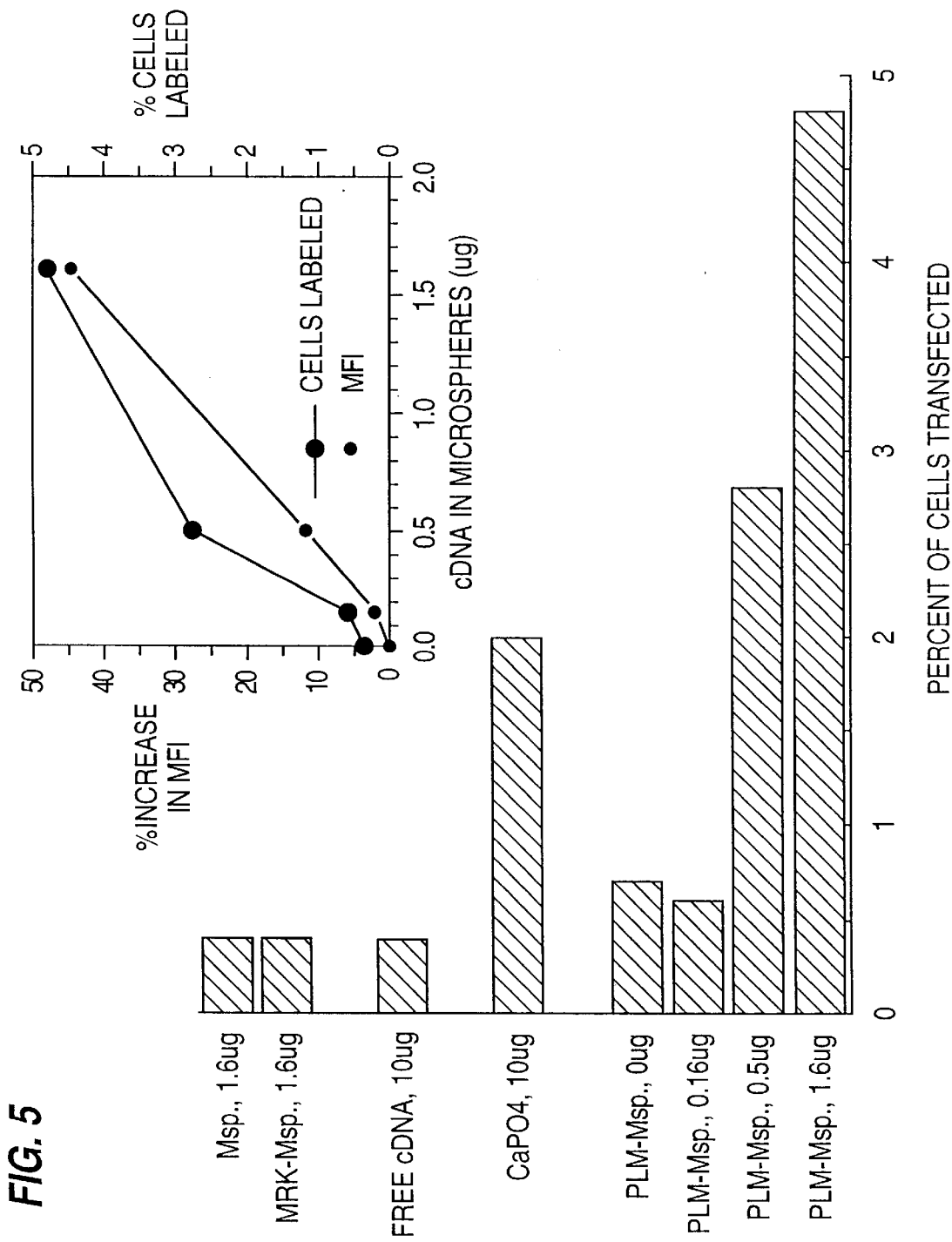
FIG. 5. Flow cytometric analysis of the transfection efficiency of U937 cells by antilymphocyte function associated antigen-1 coated microparticles and controls. The actual mean fluorescence intensity (MFI) is shown in the insert. Msp=microspheres, MRK=a mismatched anti-P-glycoprotein antibody, PLM=anti-LFA antibody.
Figure 6:
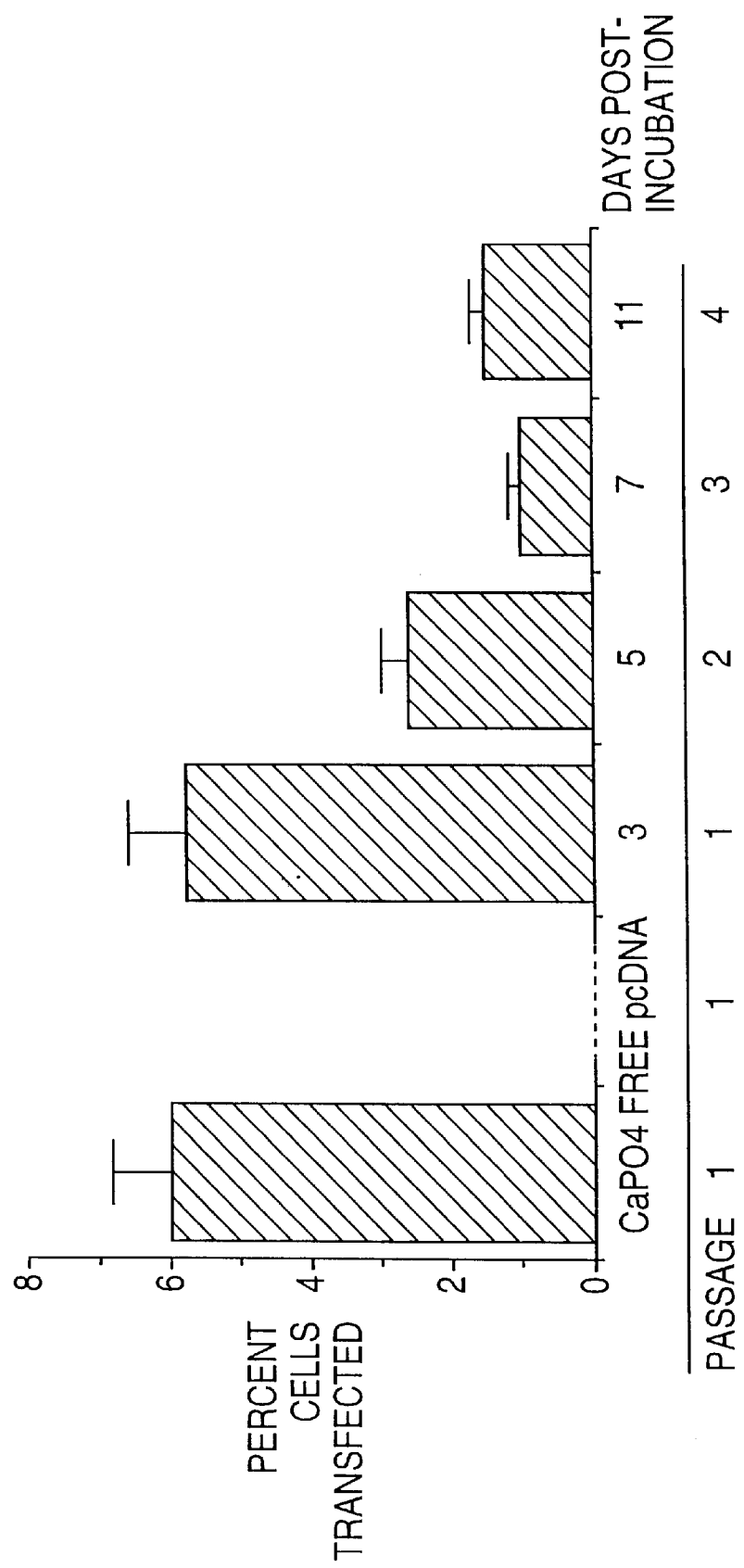
FIG. 6. Temporal expression of LAMP-1 in 293s cells transfected by anti-CD44 coated microparticles.

Using flow cytometry, we showed that the expression of LAMP-1 was detected in up to 5% of U937 cells in culture (FIG. 5). None of the controls—blank microspheres, microspheres with cDNA but no antibodies, microspheres with cDNA and coated with a mismatched anti-P-glycoprotein antibody (MRK-Msp.), and free cDNA at a concentration six time higher than entrapped in the microspheres—showed any evidence of transfection. The efficiency of transfection appears to be dose-responsive. In general, the transfection efficiency of this particular gene and cell type is comparable between the proposed microspheric delivery system (1–10%) and the calcium phosphate precipitation method (2–15%). FIG. 6 demonstrates the concept in a different cell type using a different monoclonal antibody. Again, free cDNA could not transfect the cells. Eventually the LAMP-1 expression disappeared after several passages. Positive results were also obtained for the luciferase reporter gene system. Transfection was clearly detected by measurement of luciferase enzymatic activity, in 293s cells incubated with luciferase gene-loaded microspheres.

We claim:

1. A solid microparticle for delivery of nucleic acids to and transfection of target cells comprising gelatin and nucleic acids, wherein a molecular species is attached to the surface of said microparticle, wherein the molecular species is selected from the group consisting of a targeting ligand and a linking molecule, wherein the linking molecule is selected from the group consisting of avidin, biotin, and staphylococcal protein A, and further wherein the microparticle is solid and is less than 3 μm.

2. The microparticle of claim 1 wherein the linking molecule is attached to said microparticle.

3. The microparticle of claim 2 wherein the linking molecule is covalently attached to said microparticle by means of glutaraldehyde cross-linking.

4. The microparticle of claim 2 wherein said linking molecule is avidin.

5. The microparticle of claim 4 wherein a biotinylated targeting ligand is coupled to the linking molecule.

6. The microparticle of claim 5 wherein the biotinylated targeting ligand is a biotinylated antibody.

7. The microparticle of claim 6 wherein biotin is bound to said antibody at oligosaccharide groups on the $F_C$ portion of said antibody.

8. The microparticle of claim 2 wherein a targeting ligand is coupled to the linking molecule.

9. The microparticle of claim 8 wherein said targeting ligand is selected from the group consisting of hormones, antibodies, cell-adhesion molecules, saccharides, and neurotransmitters.

10. The microparticle of claim 1 wherein the targeting ligand is attached to said microparticle.

11. The microparticle of claim 10 wherein said targeting ligand is selected from the group consisting of hormones, antibodies, cell-adhesion molecules, saccharides, and neurotransmitters.

12. The microparticle of claim 1 wherein said microparticle comprises from 5% to 30% (w/w) nucleic acids.

13. The microparticle of claim 1 wherein said microparticle comprises 20% to 30% (w/w) nucleic acids.

14. The microparticle of claim 1 wherein said nucleic acids comprises a gene larger than 10 kb.

15. The microparticle of claim 1 further comprising chondroitin sulfate.

16. The microparticle of claim 1 wherein said nucleic acids comprise a gene of 2 to 10 kb.

17. A method of forming solid microparticles for gene delivery and transfection of target cells, comprising the steps of:
   forming solid microparticles by coacervation of nucleic acids and gelatin, wherein the gelatin is at a concentration between 2% and 7%; and,
   adhering a molecular species to the surface of the microparticles wherein the molecular species is selected from the group consisting of a targeting ligand and a linking molecule, wherein the linking molecule is selected from the group consisting of avidin, biotin, and staphylococcal protein A.

18. The method of claim 17 further comprising the step of:
   cross-linking the molecular species to the microparticles.

19. The method of claim 17 wherein a linking molecule is adhered, said method further comprising the step of:
   binding a targeting ligand to the linking molecule.

20. The method of claim 19 wherein the targeting ligand is selected from the group consisting of antibodies, hormones, cell-adhesion molecules, saccharides, and neurotransmitters.

21. The method of claim 19 wherein the targeting ligand is chemically modified with a moiety which binds to the linking molecule.

22. The method of claim 17 wherein the coacervation is performed in the presence of sodium sulfate.

23. The method of claim 22 wherein the concentration of sodium sulfate is between about 7 and 43 mM in the step of coacervation.

24. The method of claim 17 wherein a targeting ligand is adhered to the surface of said microparticle, said targeting ligand being selected from the group consisting of antibodies, hormones, cell-adhesion molecules, saccharides, and neurotransmitters.

25. The method of claim 17 wherein the linking molecule is avidin.

26. The method of claim 17 wherein the nucleic acids are present in a concentration of 1 ng/ml to 500 μg/ml in the step of coacervation.

27. A method for introducing nucleic acids into cells, in vitro, comprising the steps of:
   incubating (a) cells to be transfected with (b) solid microparticles of less than 3 μm, said microparticles comprising gelatin and nucleic acids, wherein a targeting ligand is attached to said microparticles' surface, said targeting ligand binding to the surface of said cells to be transfected, whereby the cells are transfected with the nucleic acids.

28. A method for introducing nucleic acids into cells of a mammal, comprising the steps of:

administering solid microparticles of less than 3 µm to said mammal, said microparticles comprising gelatin and nucleic acids, wherein a ligand is attached to said microparticles' surface, said ligand binding to the surface of said cells, whereby said cells are transfected with said nucleic acids.

29. The method of claim 27 or 28 wherein the said ligand is attached to said microparticle's surface by means of a linking molecule.

30. The method of claim 29 wherein the linking molecule is avidin.

31. The method of claim 27 or 28 wherein the said ligand is selected from the group consisting of: antibodies, hormones, cell-adhesion molecules, saccharides, and neurotransmitters.

32. The method of claim 27 or 28 wherein the nucleic acid is DNA.

33. The method of claim 27 or 28 wherein the nucleic acid is RNA.

34. The method of claim 27 or 28 wherein the cells are muscle cells.

35. The method of claim 27 or 28 wherein the cells are epithelial cells.

36. The method of claim 35 wherein the epithelial cells are lung epithelial cells.

37. A solid microparticle for delivery of nucleic acids to and transfection of target cells comprising gelatin and a polyanion consisting of nucleic acids, wherein a molecular species is attached to the surface of said microparticle, wherein the molecular species is selected from the group consisting of a targeting ligand and a linking molecule, wherein the linking molecule is selected from the group consisting of avidin, biotin, and staphylococcal protein A, and further wherein the microparticle is solid and is less than 3 µm.

38. A method of forming solid microparticles for gene delivery and transfection of target cells, comprising the steps of:

forming solid microparticles by coacervation of a polyanion consisting of nucleic acids and gelatin, wherein the gelatin is at a concentration between 2% and 7%; and, adhering a molecular species to the surface of the microparticles wherein the molecular species is selected from the group consisting of a targeting ligand and a linking molecule, wherein the linking molecule is selected from the group consisting of avidin, biotin, and staphylococcal protein A.

39. A method for introducing nucleic acids into cells, in vitro, comprising the steps of:

incubating (a) cells to be transfected with (b) solid microparticles of less than 3 µm, said microparticles comprising gelatin and a polyanion consisting of nucleic acids, wherein a targeting ligand is attached to said microparticles' surface, said targeting ligand binding to the surface of said cells to be transfected, whereby the cells are transfected with the nucleic acids.

40. A method for introducing nucleic acids into cells of a mammal, comprising the steps of:

administering solid microparticles of less than 3 µm to said mammal, said microparticles comprising gelatin and a polyanion consisting of nucleic acids, wherein a ligand is attached to said microparticles' surface, said ligand binding to the surface of said cells, whereby said cells are transfected with said nucleic acids.

* * * * *